US007575597B2

(12) United States Patent
Rehnke

(10) Patent No.: US 7,575,597 B2
(45) Date of Patent: Aug. 18, 2009

(54) METHOD FOR SURGICAL DISSECTION, SIZING AND EXPANSION

(76) Inventor: Robert D. Rehnke, 3011 82 Way North, St. Petersburg, FL (US) 33710

( * ) Notice: Subject to any disclaimer, the term of this patent is extended or adjusted under 35 U.S.C. 154(b) by 0 days.

(21) Appl. No.: 11/974,546

(22) Filed: Oct. 15, 2007

(65) Prior Publication Data

US 2008/0035161 A1 Feb. 14, 2008

Related U.S. Application Data

(60) Continuation of application No. 11/054,401, filed on Feb. 9, 2005, now Pat. No. 7,282,062, which is a continuation of application No. 10/614,763, filed on Jul. 8, 2003, now abandoned, which is a continuation of application No. 09/525,599, filed on Mar. 14, 2000, now abandoned, which is a division of application No. 08/865,824, filed on May 30, 1997, now Pat. No. 6,055,989, which is a continuation-in-part of application No. 08/622,341, filed on Mar. 21, 1996, now abandoned.

(51) Int. Cl.
*A61F 2/12* (2006.01)
(52) U.S. Cl. .......................................... 623/8; 606/190
(58) Field of Classification Search ................. 128/898; 623/7, 8, 902; 606/192, 190; 604/96
See application file for complete search history.

(56) References Cited

U.S. PATENT DOCUMENTS

| | | | |
|---|---|---|---|
| 3,994,301 A | 11/1976 | Agris | |
| 4,157,085 A | 6/1979 | Austad | |
| 4,217,889 A | 8/1980 | Radovan et al. | |
| 4,624,671 A | 11/1986 | Kress | |
| 4,685,447 A | 8/1987 | Iversen et al. | |
| 4,823,815 A | 4/1989 | Watson et al. | |

(Continued)

OTHER PUBLICATIONS

Spacemaker Surgical Balloon Dissector, Guide Rod with Balloon Cartridges, Model No. PSD 1915-01.

(Continued)

*Primary Examiner*—William H. Matthews

(57) ABSTRACT

A method for surgical dissection, sizing and for expansion of a tissue pocket in a naturally occurring fascial cleft is disclosed for use in plastic surgery applications and other applications where it is desirable to dissect an anatomically defined and bounded tissue pocket, determine the appropriate size of a prosthesis to be implanted into the tissue pocket and, if necessary, further expand the tissue overlying the tissue pocket. An inflatable device which performs the three distinct functions of dissection, sizing and tissue expansion is used. In a preferred method, a dissecting balloon device is tunneled bluntly to a desired location within a fascial cleft in the female breast. The device is then inflated to dissect tissue layers adjacent the fascial cleft until ligaments defining boundaries of the fascial cleft are reached, to create a tissue pocket extending to the ligmentous boundaries. After dissection, the tissue pocket may be sized by withdrawing/adjusting fluid from the inflatable member until the desired aesthetic appearance is achieved. If immediate or traditional tissue expansion is desired, the inflatable member may be utilized as a tissue expander and temporarily left in place to provide gradual tissue expansion. After the desired dissection, sizing and optional expanding, an implant prosthesis may be inserted into the tissue pocket and filled to a volume determined in the sizing step.

15 Claims, 5 Drawing Sheets

U.S. PATENT DOCUMENTS

| | | |
|---|---|---|
| 4,955,905 A | 9/1990 | Reed |
| 5,092,348 A | 3/1992 | Dubrul et al. |
| 5,158,571 A | 10/1992 | Picha |
| 5,163,949 A | 11/1992 | Bonutti |
| 5,258,026 A | 11/1993 | Johnson et al. |
| 5,411,554 A | 5/1995 | Scopelianos et al. |
| 5,496,345 A | 3/1996 | Kieturakis et al. |
| 5,500,019 A | 3/1996 | Johnson et al. |
| 5,514,153 A | 5/1996 | Bonutti |
| 5,630,813 A | 5/1997 | Kieturakis |
| 5,655,545 A | 8/1997 | Johnson et al. |
| 5,658,328 A | 8/1997 | Johnson |
| 5,690,668 A | 11/1997 | Fogarty et al. |
| 5,702,417 A | 12/1997 | Hermann |
| 5,776,159 A | 7/1998 | Young |
| 5,871,497 A | 2/1999 | Young |
| 6,055,989 A | 5/2000 | Rehnke |

OTHER PUBLICATIONS

Spacemaker Surgical Balloon Dissector with Responsible Guide Rod, Instructions For Use, 1996.

Ferraro et al., Improving the Efficiency, Ease, and Efficacy of Endoscopic Abdominoplasty, p. 895-898, Mar. 1997.

Levin et al., Endoscopy of the Upper Extremity, vol. 11, No. 1, Feb. 1995, p. 59-70.

MDI, Inside Surgery, vol. II: No. 4, Oct. 1994.

Buskirk, et al., Endoscopic Harvest of the Latissimus Dorsi Muscle Using the Balloon Dissection Technique, p. 899-903, Mar. 1997.

METHOD FOR SURGICAL DISSECTION, SIZING AND EXPANSION

RELATED APPLICATIONS

This application is a continuation of U.S. patent application Ser. No. 11/054,401, filed on Feb. 9, 2005, now U.S. Pat. No. 7,282,062 which is a continuation of U.S. patent application Ser. No. 10/614,763, filed on Jul. 8, 2003, now abandoned, which is a continuation of U.S. patent application Ser. No. 09/525,599, filed on Mar. 14, 2000, now abandoned, which is a division of U.S. patent application Ser. No. 08/865,824, filed on May 30, 1997, now U.S. Pat. No. 6,055,989, which is a continuation-in-part of U.S. patent application Ser. No. 08/622,341, filed on Mar. 21, 1996, now abandoned. The disclosures of which are hereby incorporated by reference in its entirety.

BACKGROUND OF THE EWENTION

1. Field of the Invention

The present invention pertains generally to the field of surgical methods for use of apparatus in-opening an anatomic space with the option of sizing and/or further expanding the dissected space. More particularly, the present invention pertains to surgical methods of dissection, sizing and expansion wherein a balloon device combines the functions of dissection, sizing, and, optionally tissue expansion.

2. Description of the Related Art

In the past, inflatable devices have been utilized to dissect tissue layers to create an anatomic working space to facilitate the performance of laparoscopic or other minimally invasive surgical procedures. For example, in U.S. Pat. No. 5,163,949, to Bonutti, the disclosure of which is hereby incorporated by reference in its entirety, various inflatable devices are disclosed which can be utilized to dissect tissue and create an anatomic working space. A surgical balloon dissector and method of use is also disclosed in U.S. Pat. No. 5,496,345, to Kieturakis et al., the disclosure of which is also hereby incorporated by reference in its entirety. It has been found that a tissue pocket formed by balloon dissection may be more regular and precise than with manual dissection. In contrast to traditional blunt dissection techniques, the dissection balloon creates the tissue pocket while respecting natural tissue planes or boundaries in the anatomy.

A second type of inflatable device, known as a tissue expander, has been utilized as temporary implants to gradually expand a previously dissected pocket over time as the overlying skin and tissue gradually alters (through new cell formation) and expands in response to the force of the tissue expander. In the tissue expander art, it is known that excessive inflation pressures in the expander can cause the undesirable result of tissue necrosis and hence the inflation pressure of the tissue expander must be precisely regulated to avoid necrosis. Because the pressure must be held beneath this pressure level, it is necessary for tissue expanders to be left in place over a prolonged period of time to allow the cutaneous tissues to gradually alter and expand. This requires precise monitoring and periodic adjustment of the expander pressure as the tissue gradually expands over time.

In certain surgical procedures, especially in plastic surgery procedures, it is necessary to dissect a tissue pocket for the later implantation of a prosthetic device. For example, breast augmentation and reconstruction procedures involve dissecting a space or pocket in the breast, sizing the space to assess later appearance and, if necessary, providing tissue expansion in order to achieve the desired aesthetic appearance. The purpose of the sizer is to provide the physician with a visual check or confirmation of the likely final appearance of the breast after the implantation is complete. Previously, two or more different devices have been required to perform the dissection, sizing and expanding steps.

Typically, the breast pocket is manually dissected through the use of a blunt instrument or the surgeons finger. A sizer may then be inserted into the manually dissected space to assess the appearance. If necessary, further manual dissection or tissue expanders are then used to adjust the pocket.

In Johnson et al., U.S. Pat. No. 5,258,026, a surgical procedure for breast augmentation is disclosed, whereby an incision is made in the umbilicus and an elongate hollow tube is introduced into the incision and pushed along the chest wall to form a tunnel to a position behind the breast. The prosthesis is then pushed into the tunnel toward its position behind the breast. In Johnson, the prosthesis itself is utilized as a tissue dissector by overinflating it to 150% of its anticipated ultimate fill volume to create the breast pocket. The prosthesis is then reduced in volume to its intended final volume and left in place. The umbilical incision is then closed and the surgery completed. While Johnson discloses the use of an inflatable member to create a tissue pocket in the breast for the purpose of augmentation, Johnson uses the implant itself to dissect and does not provide a device or method for arbitrarily sizing the tissue pocket after it is dissected or for further expanding the tissue pocket should the size of the initially dissected space be insufficient. In addition, prosthesis manufacturers do not wish their implants to be overinflated as Johnson describes because it may compromise the implant's integrity.

Accordingly, there is a need for improved methods of surgical dissection, sizing and expansion to overcome the aforementioned disadvantages in the prior art.

SUMMARY OF THE INVENTION

The present disclosure provides a surgical method of performing any combination of the distinct functions of dissecting, expanding, and sizing in serial order. The method preferably utilizes a nonelastic balloon formed from a urethane material, for example, to dissect tissue layers to open a tissue pocket or working space, to provide serial tissue expansion and if necessary to thereafter size the dissected space.

In a preferred method of use directed to plastic surgery applications a combination device comprising a balloon dissector is introduced, preferably by blunt tunneling, to a location where it is desired to create a tissue pocket. The balloon associated with the device is then inflated to dissect tissue layers along natural tissue planes until the natural cleft being dissected has reached one or more natural fascial boundaries thereby creating a tissue pocket defined by natural tissue planes and fascial boundaries. In plastic surgery applications involving implants, such as breast augmentation or reconstruction, after dissection, the tissue pocket may be sized by withdrawing inflation fluid from the balloon until the desired appearance for the augmented breast is achieved and implant fill volume can be predicted. The creation of space in naturally occurring fascial clefts limited by fascial boundaries has application to a variety of anatomical locations such as the head, forearm, legs, abdomen, chest, etc. for a variety of reasons. For example, a space may be dissected in a fascial cleft to the natural ligamentous boundary in a forearm, and thereafter, the balloon may be utilized as a tissue expander and left in the body over a period of time to achieve gradual tissue expansion.

These and other aspects, features, objects, and advantages of the present invention will be more fully understood and

DETAILED DESCRIPTION OF PREFERRED EMBODIMIENTS

Figure 1:
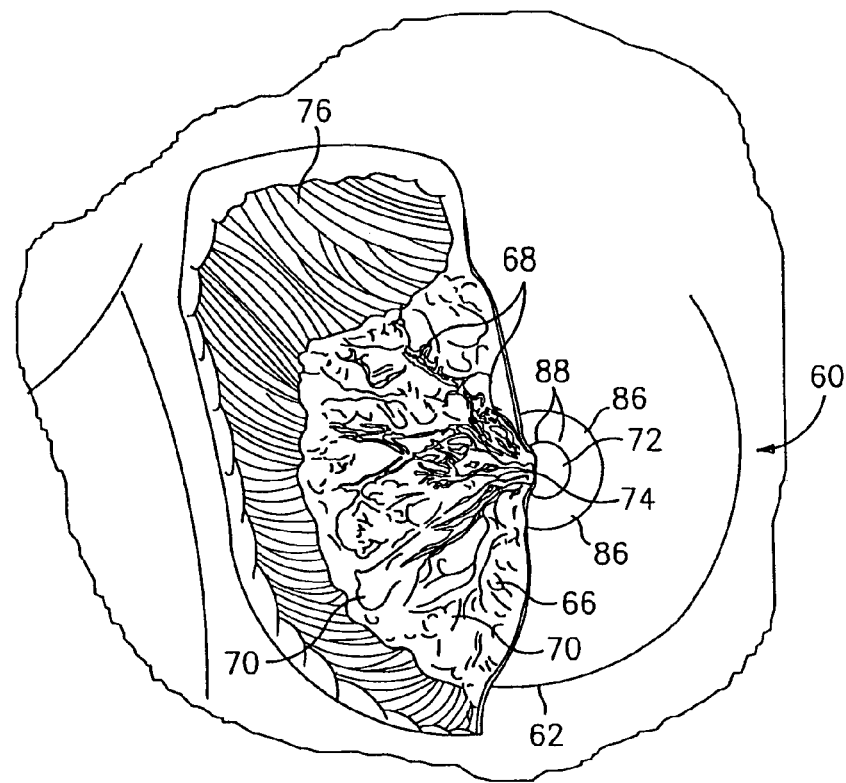
FIG. 1 is a front view of the anatomy of the human breast with a portion shown in subcutaneous detail.

While some ligaments joining fascia and skin have been described, such as the inframammary ligament in the breast, it has found that the understanding of such ligaments has previously been incomplete, and that in certain areas of the body points of fusion between layers of fascia create well-defined boundaries which may be used to advantage by the surgeon during dissection, particularly balloon dissection, to create an anatomically well-defined space between layers joined by such ligaments. Ligaments have been identified which create such useful boundaries in, for example, the breast, forearm, leg, and brow. A more complete description of how a surgeon may use these well-defined boundaries will be given with respect to breast augmentation or reconstruction, but skilled surgeons, particularly plastic surgeons, will understand that the principles described herein have application to any bodily region where such fascial boundaries exist. Moreover, skilled surgeons will understand that the principles described herein have application to various other surgical procedures (e.g., treatment of carpal tunnel syndrome).

As pointed out above, certain ligaments connecting fascia to skin and other tissue in the female breast are known and previously have been described. These include, for example, the inframammary ligament and the vertical cutaneous ligaments. However, it has been found that the mammary ligaments form a circumferential ligament about the breast to form a circumferential fusion between the superficial fascia and the deep fascia. This connective ligament which completely surrounds the breast to form a circular boundary to the cleft between the superficial fascia and deep fascia is referred to herein as the "circumferential mammary ligament". As described in greater detail below, because the circumferential mammary ligament forms a natural boundary connecting two tissue layers, a surgeon dissecting between the layers may use the natural boundary to advantage to both define and limit the extent of the dissection between the layers. In particular, a surgeon can define and limit the extent of dissection using a dissection balloon. While this technique is described in connection with the circumferential mammary ligament, the technique of the preferred method has application wherever natural boundaries are by boundary-defining connective tissue extending between tissue layers to be dissected, including between the chest wall and the pectoralis major muscle.

Breast augmentation has traditionally been performed using one of two types of implants—silicone and saline. Saline implants are filled at the time of surgery with saline solution which is not felt to be harmful if rupture or leakage of the implant takes place. They can be inserted through very small incisions in a deflated form and after they are in place in 'the body, can be inflated to their final size. Saline implants however, are firmer and more noticeable beneath thin soft tissue coverage and therefore, in most instances require placement underneath the pectoralis major muscle (sub pectoral placement). This adds to the length of the surgical procedure and time for surgical recovery. New implants are on the horizon, one of which are soybean oil filled implants. They have the promise of a softer, more natural appearance and feel with positioning in the sub glandular position, but come in a deflated form similar to the saline implants and therefore can be placed through small incisions.

While the present disclosure is principally described in terms of breast augmentation, it may also be used in connection with other surgical procedures, including, but not limited to, brow lifts, traditional tissue expansion, endoscopic treatment of carpal tunnel syndrome and endoscopic abdominoplasty.

In a first preferred method of use, a device which is capable of both dissecting and sizing may, for example, be any one of a variety of balloon dissectors, such as Spacemaker™ balloon dissection devices available from General Surgical Innovations (GSD and balloon dissection devices available from Origin Medical Systems, provided that when the fluid volume is reduced appropriately after dissection, the state of fill of the balloon remains adequate to assume a sufficiently determinate shape to be effective for use in sizing. The balloon may be carried by or otherwise associated with a tunneling member, such as being rolled or folded about the tunneling member. The tunneling member may be a rod or, if visualization is desired, may be a hollow tube adapted to receive a laparoscope. By utilizing a combination device, a single balloon may be used to create a tissue pocket between adjoining tissue layers and thereafter to size the dissected pocket.

In the preferred method, an incision is first made in the body at a location appropriate for the procedure and the combination device with a deflated, rolled balloon is tunneled bluntly to a desired location within the body. In the case of breast augmentation or reconstruction, for example, several different incision sites may be appropriate depending on the surgical approach utilized as described below.

Figure 2:
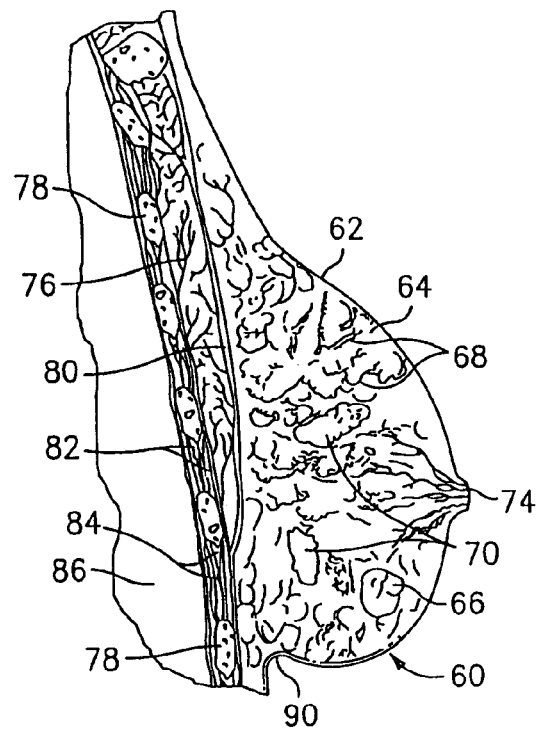
FIG. 2 is a cross-sectional side view of the anatomy of the human breast including the subcutaneous layers down to the rib cage.

Referring initially to FIGS. 1 and 2, front and side views of the anatomy of the human breast 60 are illustrated. An epidermis layer 62 overlies the dermis layer 64. Underneath the dermis layer 64 is a layer of subcutaneous fat 66. Suspensory ligaments 68 are positioned within the layer of subcutaneous fat 66 to hold breast 60 in an upright position. Gland lobules 70 are arranged radially about the nipple 72. Each gland lobe 70 has its own lactiferous duct 74 opening on the nipple 72. Nipple 72 is surrounded by areola 88. The pectoralis major muscle 76 covers the chest wall and ribs 78, and is covered by a layer of superficial fascia 80. Intercostal muscles 82 are shown situated between ribs 78 and surrounding intercostal vessels and nerve 84. The lung 86 is positioned behind ribs 78.

Figure 3:
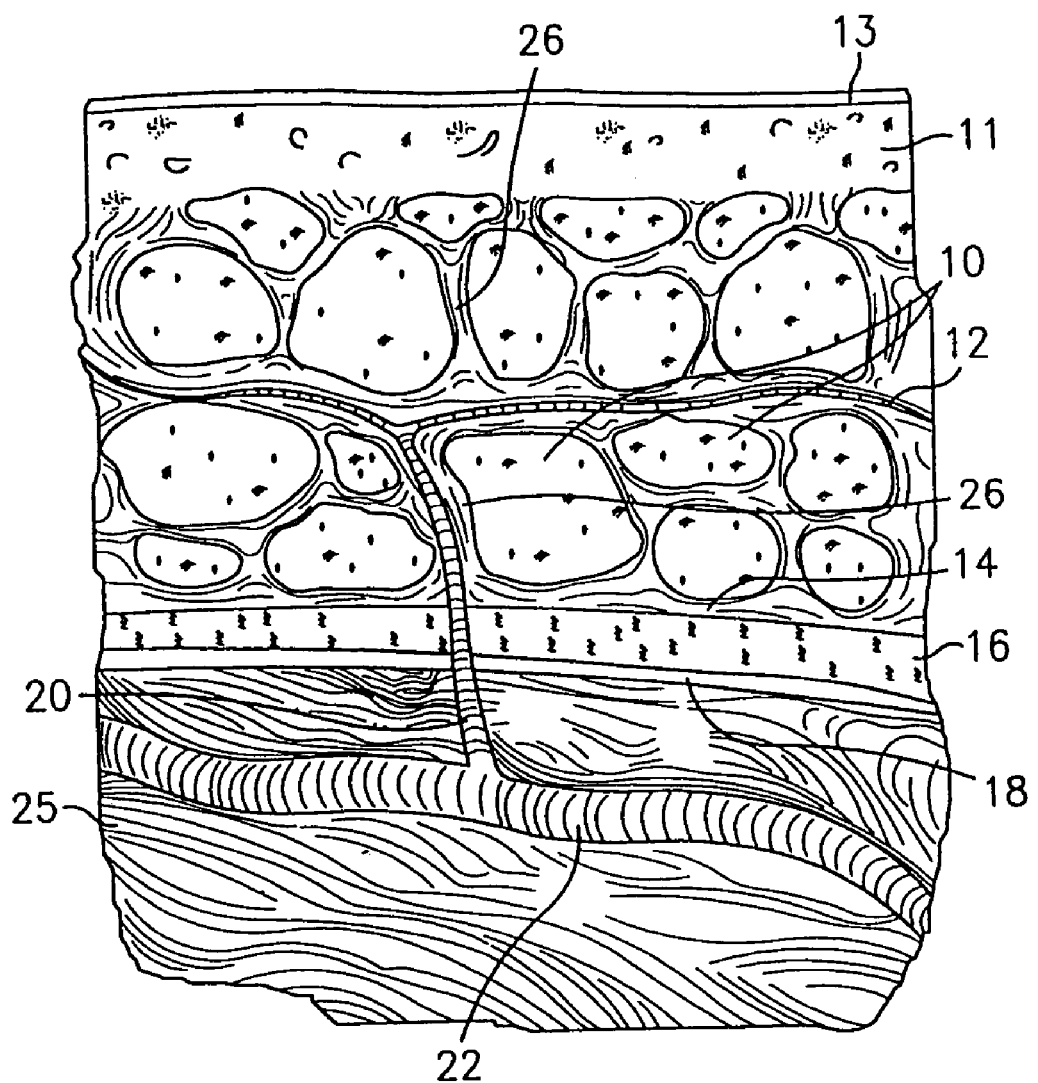
FIG. 3 is a cross-sectional view of a portion of the human anatomy, illustrating the fascial cleft between the superficial fascia and deep fascia.

Turning now to FIG. 3, a cross-sectional view of the anatomy of the human cutaneous tissue particularly illustrating a fascial cleft between the superficial fascia and the deep fascia. An epidermis layer 13 overlies the dermis layer 11. Underneath the dermis 11 is a layer of subcutaneous fat 10. Superficial vessels 12 within the fat layer 10 are connected to perforating vessels 20 which in turn are connected to deep vessels 22. Vertical cutaneous ligaments 26. joining tissue layers, are also shown within the fat layer 10. Muscle 25 is covered by a thin layer of deep fascia 18. The fat layer 10 is sheathed by a thin layer of superficial fascia 14. A naturally occurring tissue plane or fascial cleft 16 (shown as a gap in FIG. 3; however, prior to dissection no gap exists) occurs between the superficial fascia 14 and deep fascia 18. This fascial cleft may be viewed as a naturally occurring potential space within the human body which may be fluently dissected by dissecting balloons to create an anatomic cavity. It has been found that the ligaments joining these tissue layers define the boundaries of the potential space and naturally limit the potential space created during balloon dissection.

Figure 4:
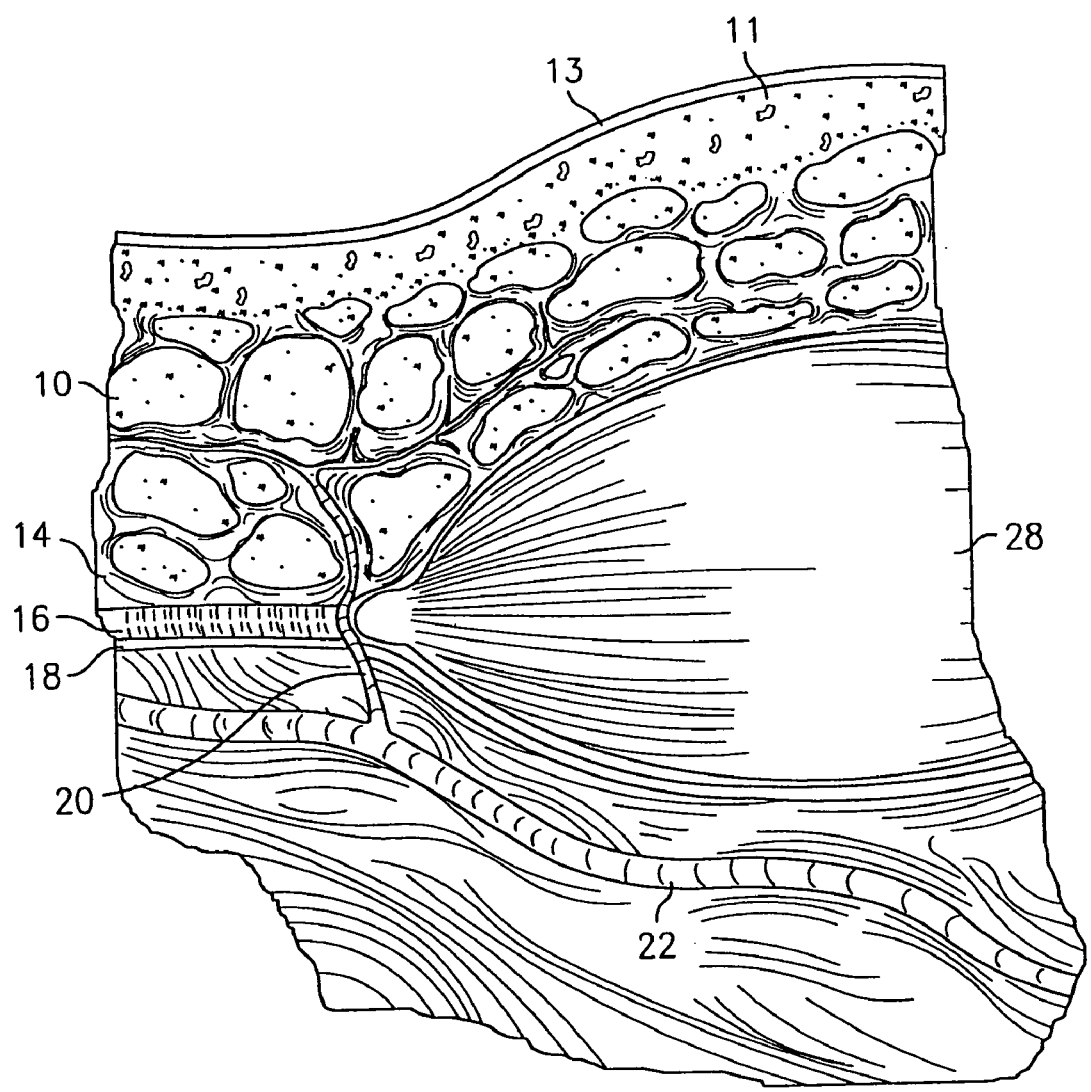
FIG. 4 is a cross-sectional view of the human cutaneous tissue, particularly illustrating a balloon dissector being utilized to form a tissue pocket between the superficial fascia and deep fascia.
Figure 5:
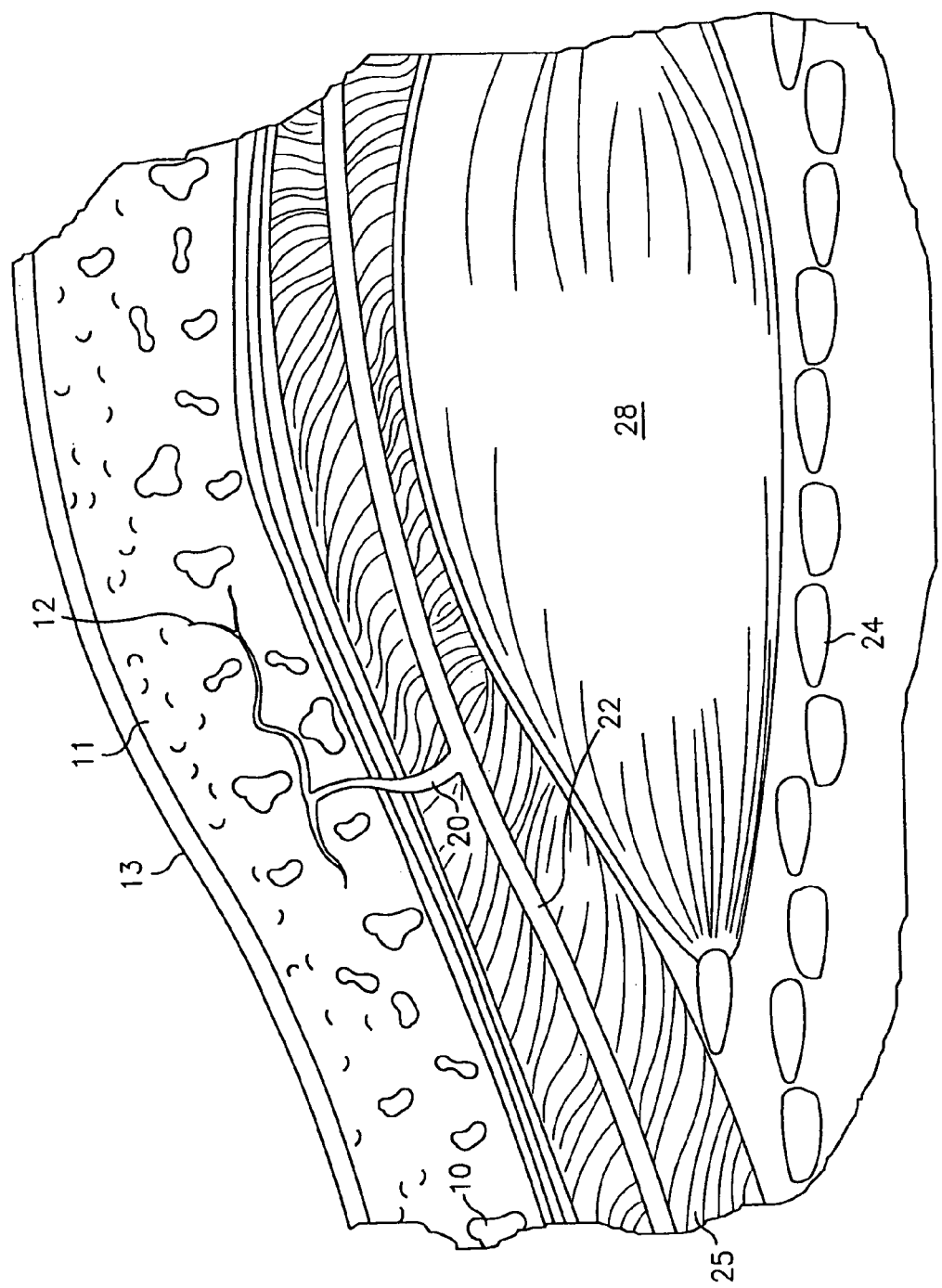
FIG. 5 is a view similar to FIG. 4 illustrating a balloon dissector being utilized in accordance with the method of the present disclosure to form a tissue pocket between the chest wall and the pectoralis major muscle overlying the chest wall.

One approach in breast augmentation is to make an axillary incision and to tunnel medially and interiorly from the axillary incision to a desired location underlying the glandular breast tissue, either between the chest wall and pectoralis major muscle or between the pectoralis major and the breast gland. When a subglandular implant is desired, the combination device 28 is preferably advanced into the naturally occurring potential space between the superfascial fascia 14 and deep fascia 18. (See FIG. 4). This path between the superficial fascia and the deep fascia defines a naturally occurring tissue plane. Dissection along such naturally occurring tissue planes is desirable in that a virtually bloodless space may be created between the tissue planes. If a subpectoral implant is desired, the combination device 28 can be tunneled bluntly below the pectoralis major muscle 25 and above the chest wall to the desired location below the breast as shown in FIG. 5.

A second technique in breast augmentation is to access the breast tissue through the inframammary fold adjacent the breast. The inframammary fold is designated as reference numeral 90 in FIG. 2. In this case, an inframammary incision is made and the combination device is tunneled superiorly into the breast tissue to a position behind the breast. The device follows either the path between the superficial and deep fascia (for a subglandular implant) or, between the chest wall and the pectoralis major muscle (for a subpectoral implant). (See FIGS. 4 and 5).

Another approach in breast augmentation is to make an incision in the periphery of the areola. A combination device may be inserted through the incision and guided adjacent a vertical cutaneous ligament to the desired location behind the breast for dissection in one of the locations described above. One advantage of this approach is that the periphery of the areola is a natural access to an advantageous fascial cleft.

After the deflated, rolled balloon has been properly positioned in either the subglandular or subpectoral position, the balloon is inflated by introducing a suitable inflation medium, such as saline solution for example, through a balloon inflation lumen into the interior of the balloon. The balloon is then filled with a sufficient amount of fluid to cause the balloon to dissect tissue layers and create the desired pocket for the implant. In the preferred method, the balloon is inflated to a size substantially larger than the expected implant size in order to cause the balloon to dissect the tissue plane fully to the circumferential ligament margin, such as the circumferential mammary ligament as defined. This preferred step in the method allows for immediate tissue expansion, wherein the device is overfilled and remains in place for a few minutes, e.g., 15; to 20; minutes, so as to stretch the tissues of the fascial cleft without disrupting the anatomic boundaries. By way of example, if a 400; cc implant is expected, it is contemplated that the balloon dissector would be inflated to 700; to 800; cc to assure that the balloon dissects the plane all the way to the margin defined in all directions by the circumferential mammary ligament. If, a balloon dissecting device with a cannula is used, an optical scope may be inserted to inspect the dissection, i.e., to confirm that the dissection has reached the circumferential mammary ligament.

After the balloon has been inflated and tissue dissection has occurred, the surgeon may thereafter withdraw a suitable amount of fluid from the balloon to visualize or size the external contour of the breast for later insertion of an equivalent volume implant. During this sizing step, the patient may be positioned in an upright manner for an intraoperative view so that the surgeon may better observe the aesthetic appearance of the augmentation or reconstruction. It is to be noted that the fill volume associated with the sizer stage of this procedure is typically less than one-half to two-thirds the fill volume needed for dissection. The fill volume for the sizing stage of the procedure is then recorded and used to later fill the prosthesis. Thereafter, the dissecting sizing balloon may be removed and, if desired, the space may be inspected by inserting an optical scope directly through the incision. An implant prosthesis is then inserted into the space which has been dissected, and filled to the volume determined in the sizing step using the balloon dissector/sizer.

In an alternate method of use, having particular application to surgical methods such as skin grafting, the balloon dissector may be utilized as a combination dissector/expander to create a tissue pocket by dissection as previously described and then leave the device in place over an. extended period of time, e.g., days, weeks or months, to gradually expand the dissected tissue pocket in a manner similar to traditional tissue expander devices. That is, the balloon is periodically filled further to cause the tissue to propagate and expand thereby creating a larger space. In this alternative method, it is contemplated that the tissue dissector/expander would be left in place over the amount of time required to achieve the desired amount of tissue expansion as is known in the tissue expander art. With regard to the tissue expansion step, it is desirable that the internal pressure of the inflatable member utilized not exceed about 18; millimeters of mercury, as pressures in excess of this range may collapse the venous system, possibly leading to tissue necrosis. It is to be noted that with traditional tissue expanders, an incision overlying the tissues to be expanded is made to insert the expander and then after the expander is inserted, the incision must be allowed to heal to prevent the incision from being reopened by the force of the tissue expander. In contrast, in accordance with the present invention, the sizer may be tunneled in from a remote incision to a desired location where tissue expansion is to occur. This allows immediate tissue dissection of the pocket and then immediate initiation of expansion without the need to permit a local incision to heal.

Figure 6:
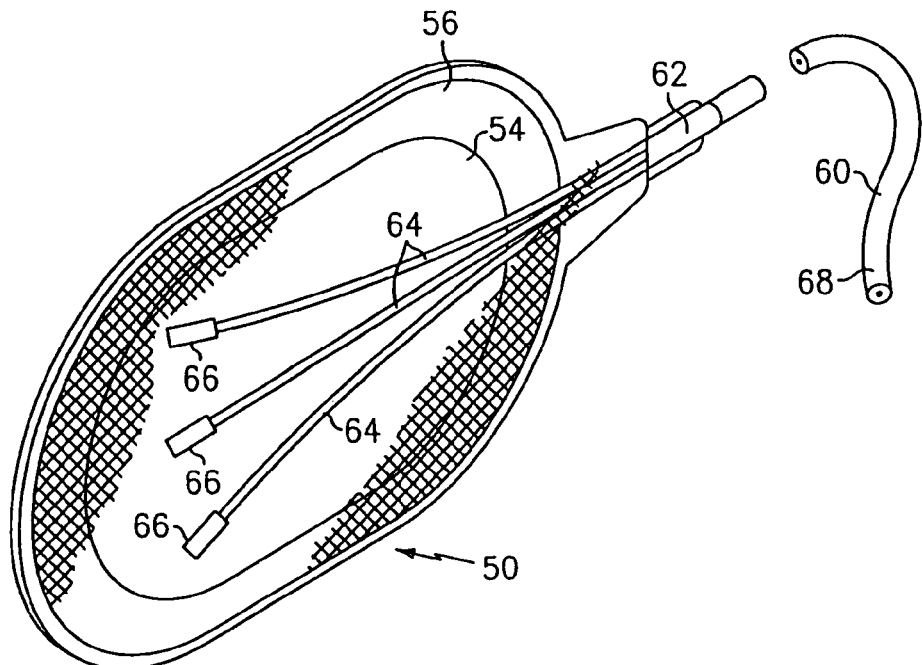
FIG. 6 is a perspective view of an exemplary inflatable device used in accordance with the present invention.
Figure 7:
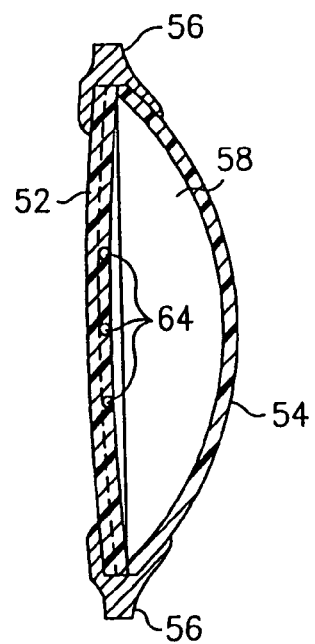
FIG. 7 is a side view of the inflatable device illustrated in FIG. 6.

Inflatable devices utilized in accordance with the method of the present invention are known in the art. Exemplary inflatable devices are disclosed, for example, in U.S. Pat. No. 4,685,447; to Iverson et al. and U.S. Pat. No. 4,823,815; to Watson et al., the disclosures of which are hereby incorporated by reference in their entirety. As illustrated in FIGS. 6 and 7, a typical inflatable device 50 generally includes a base 52, an expansion layer 54—and joined overlapping washers 56 joining the base 52 and the expansion layer 54 to form an expansion chamber 58. A fill tube 60 provides a passage for fluid, such as air or saline fluid, to be forced into the expansion chamber 58. Fill tube 60 has an end portion 62 that extends between base 60 and expansion layer 54. A plurality of fluid supply passages 64 are provided in the base and communicate with end portion 62 of fill tube 60 and extend through the base to wells 66 which communicate with chamber 58. The tube 60 at an opposite end 68 is in fluid communication with an injection site (not shown).

In actual use, the inflatable device may be rolled or folded and carried by a tunneling device, such as a rod, which may be disposable or reusable. The inflatable device is advanced bluntly to a desired location within the body. A tissue pocket may be created by introducing saline solution through fill tube 60 into the interior space defined by base 60 and expansion layer 54 of the expandable device. After the device has been inflated to dissect the tissue pocket, the inflation fluid may be withdrawn from the interior space through the fill tube 60 by suction to achieve a proper sizing volume.

After the sizing step is complete, if it is necessary to further expand the dissected pocket, device 50 may be inflated by introducing saline solution through fill tube 60 into the interior space defined by base 52 and expansion layer 54. After device 50 has been inflated to provide a semi-rigid and well-defined structure lying against the bottom or posterior side of the dissected space, it is again gradually inflated through fill tube 60 observing the appropriate pressure regimes utilized in tissue expansion. Device 50 may then be left in the dissected pocket over a period of time as a tissue expander. The internal pressure of device 50 will need to be periodically adjusted as the tissue gradually expands over time. After the desired amount of tissue expansion has occurred, device 50 may be removed by suctioning the inflation fluid from the interior space through fill tube 60. The sizing step may be repeated. Device 50 is then removed from the body, and a suitable prosthesis is implanted.

Having thus described various embodiments, it will be understood by those skilled in the art that many applications of the invention will suggest themselves without departing from the spirit and scope of the invention. For example, the methods herein described may be used in a wide variety of application where fascial clefts or planes or potential spaces occur in the anatomy.

Thus, the disclosure and the description herein are purely illustrative and are not intended to be in any sense limiting.

What is claimed is:

1. A surgical method comprising the steps of:
making an incision through skin of a patient;
inserting a device through the incision, the device including a non-elastic inflatable portion;
positioning the device to access a desired fascial cleft between tissue layers;
inflating the inflatable portion of the device to dissect the tissue layers along naturally occurring tissue planes to the limits of fascial boundaries defining the fascial cleft;
deflating the inflatable portion of the device; and
removing the device through the incision.

2. The surgical method of claim 1 further comprising the step of:
predicting a desirable size of a prosthesis to be implanted into the fascial cleft.

3. The surgical method of claim 2, wherein the inflatable portion is partially deflated to assess a potential size of a prosthesis to be implanted.

4. The surgical method of claim 1 further comprising the step of:
inserting a prosthesis after removal of the device.

5. The surgical method of claim 4 wherein the prosthesis includes a fluid filled implant and wherein the prosthesis is filled after insertion with an amount of fluid determined during said sizing step.

6. The surgical method of claim 1 wherein said dissecting step comprises immediately expanding the expanding device to a volume which is about two times larger than the volume of an intended prosthesis.

7. The surgical method of claim 1 wherein said dissecting step includes periodic fluid addition over a period of time to permit a space between the dissected tissue layers to gradually alter and expand.

8. The surgical method of claim 1 wherein a tissue pocket is created in a fascial cleft occurring between superficial and deep fascia in a human breast.

9. The surgical method of claim 1 wherein a tissue pocket is created between a chest wall and a pectoralis major muscle in a human breast.

10. The surgical method of claim 2 further including the steps of:
observing the external contour of the skin; and
adjusting the volume of the device until a desired cosmetic appearance is obtained and noting the fill volume associated with the desired cosmetic appearance.

11. The surgical method of claim 1 wherein the incision is made in an inframammary fold adjacent a human breast.

12. The surgical method of claim 1 wherein the incision is made in an axilla area of a human body.

13. The surgical method of claim 1 wherein the incision is made at the periphery of an areola of a human breast.

14. The surgical method of claim 1 wherein a tissue pocket is defined by ligaments defining the fascial cleft.

15. The surgical method of claim 14 wherein the tissue pocket is substantially bloodless.

* * * * *